United States Patent
Kramer

(10) Patent No.: US 7,616,871 B2
(45) Date of Patent: Nov. 10, 2009

(54) WATER CHAMBER FOR HUMIDIFIER

(75) Inventor: Martin Paul Friedrich Kramer, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 327 days.

(21) Appl. No.: 10/568,517

(22) PCT Filed: Aug. 12, 2004

(86) PCT No.: PCT/NZ2004/000182

§ 371 (c)(1),
(2), (4) Date: Feb. 12, 2007

(87) PCT Pub. No.: WO2005/018724

PCT Pub. Date: Mar. 3, 2005

(65) Prior Publication Data

US 2007/0230927 A1    Oct. 4, 2007

(30) Foreign Application Priority Data

Aug. 20, 2003   (NZ) .................................. 527734

(51) Int. Cl.
*A61H 33/12*    (2006.01)
(52) U.S. Cl. .................. 392/403; 392/386; 392/402
(58) Field of Classification Search .......... 392/386–406
See application file for complete search history.

(56) References Cited

U.S. PATENT DOCUMENTS

| | | | |
|---|---|---|---|
| 4,013,742 A * | 3/1977 | Lang | 261/130 |
| 4,060,576 A | 11/1977 | Grant | |
| 4,110,419 A | 8/1978 | Miller | |
| 4,152,379 A * | 5/1979 | Suhr | 261/142 |
| 4,172,105 A | 10/1979 | Miller et al. | |
| 4,487,746 A * | 12/1984 | Tahiliani | 422/170 |
| 4,500,480 A | 2/1985 | Cambio, Jr. | |
| 4,588,425 A | 5/1986 | Usry et al. | |
| 4,640,804 A | 2/1987 | Mizoguchi | |
| 4,676,237 A | 6/1987 | Wood et al. | |
| 4,722,334 A | 2/1988 | Blackmer et al. | |
| 4,829,998 A | 5/1989 | Jackson | |
| 4,921,642 A | 5/1990 | LaTorraca | |
| 4,941,469 A | 7/1990 | Adahan | |
| 5,031,612 A | 7/1991 | Clementi | |
| 5,062,145 A | 10/1991 | Zwaan et al. | |
| 5,148,801 A | 9/1992 | Douwens et al. | |
| 5,231,979 A | 8/1993 | Rose et al. | |
| 5,336,156 A | 8/1994 | Miller et al. | |

(Continued)

FOREIGN PATENT DOCUMENTS

DE        719 077        3/1942

(Continued)

*Primary Examiner*—Thor S Campbell
(74) *Attorney, Agent, or Firm*—Trexler, Bushnell, Giangiorgi, Blackstone & Marr, Ltd.

(57) ABSTRACT

A water chamber (1) adapted for use in conjunction with a heater base, for humidifying an air stream. The chamber (1) including at least one horizontally oriented gases port (3) including an elongate flow tube (5) extending into the chamber (1) from the inner periphery of the gases port (3), the flow tube (5) having an opening at its distal end facing a direction transverse to the axis of the tube (5).

7 Claims, 4 Drawing Sheets

U.S. PATENT DOCUMENTS

| | | | |
|---|---|---|---|
| 5,529,060 A | 6/1996 | Salmon et al. | |
| 5,558,084 A | 9/1996 | Daniell et al. | |
| 5,564,415 A | 10/1996 | Dobson et al. | |
| 5,588,423 A | 12/1996 | Smith | |
| 5,640,951 A | 6/1997 | Huddart et al. | |
| 5,673,687 A | 10/1997 | Dobson et al. | |
| 5,991,507 A | 11/1999 | Bencsits | |
| 6,024,694 A | 2/2000 | Goldberg et al. | |
| 6,050,260 A | 4/2000 | Daniell et al. | |
| 6,095,505 A | 8/2000 | Miller | |
| 6,394,084 B1 | 5/2002 | Nitta | |
| 6,397,841 B1 | 6/2002 | Kenyon et al. | |
| 6,398,197 B1 * | 6/2002 | Dickinson et al. | 261/141 |
| 6,474,335 B1 | 11/2002 | Lammers | |
| 6,718,974 B1 | 4/2004 | Morberg | |
| 6,918,389 B2 | 7/2005 | Seakins et al. | |
| 6,983,749 B2 * | 1/2006 | Kumar et al. | 128/204.15 |
| 2003/0131844 A1 * | 7/2003 | Kumar et al. | 128/200.24 |
| 2006/0174889 A1 * | 8/2006 | Noble | 128/206.11 |
| 2007/0178030 A1 * | 8/2007 | Ross | 422/305 |

FOREIGN PATENT DOCUMENTS

| | | |
|---|---|---|
| DE | 10226160 | 1/2004 |
| JP | 05317428 | 12/1993 |
| JP | 09234247 | 9/1997 |
| WO | WO01/10489 | 2/2001 |
| WO | WO02/066106 | 8/2002 |

\* cited by examiner

WATER CHAMBER FOR HUMIDIFIER

BACKGROUND TO THE INVENTION i) Field of the Invention

The present invention relates to water chambers for gases humidification and in particular to water chambers for "slide-on" humidifiers and CPAP machines.

ii) Summary of the Prior Art

In the prior art humidification systems are well known which include a heater base and a disposable humidifier chamber which is fitted onto the heater base and within which a supply of water can be heated by the heater base. An example of such a system is described in U.S. Pat. No. 6,398,197. Air passing through the chamber from an inlet to an outlet is humidified by the evaporation of water from the water supply. It is desirable to provide a low resistance flow path for the air to be humidified, minimising pressure losses in the chamber.

Humidifier chambers of this type are also now used in compact and portable ventilation machines, for example machines intended for the home treatment of obstructive sleep apnoea (CPAP machines). These machines pose a particular difficulty as the air flow is delivered directly to the humidifier chamber from the air blower of the CPAP machine and this can generate an annoying noise level within the humidifier chamber. Furthermore where the CPAP machine is adapted for use with slide-on humidifier chambers, and the connection of the chamber to the machine is accomplished within the single sliding movement, the inlet port, or the inlet and outlet port is consequently provided horizontally through a side of the chamber. Locating the ports in the side of the chamber significantly increases the likelihood of water spillage from the chamber if the chamber is tilted with water therein. This can be of particular disadvantage where the water may flow out through the inlet port and into the air blower of the CPAP machine.

SUMMARY OF THE INVENTION

It is therefore an object of the present invention to provide a water chamber which at least goes some way towards overcoming the above disadvantages or which will at least provide the public with a useful choice.

In a first aspect the invention consists in a water chamber adapted for use in conjunction with a heater base and having at least one horizontally oriented gases port in a wall thereof the improvement comprising an elongate flow tube having a longitudinal axis extends into said water chamber from the inner periphery of said at least one gases port with an opening at a distal end of said flow tube being spaced from the wall of said chamber, said opening facing a direction transverse to the longitudinal axis of said tube at the distal end, said transverse direction not being downwards and said distal of said tube being shaped in a smooth curve to provide a barrier to water.

Preferably said chamber includes an inlet gases port and an outlet gases port, both said inlet gases port and said outlet gases port including a said elongate flow tube.

Preferably said chamber further includes a baffle between said opening of said inlet gases port tube and said opening of said outlet gases port tube.

Preferably said baffle extends from the roof of said chamber and terminates below the surface of water in said chamber when said chamber is filled to a maximum intended water level for use.

Preferably said inlet gases port and said outlet gases port includes a said elongate flow tube having an opening facing a direction transverse to an axis of said tube, said opening of said inlet flow tube and said opening of said outlet flow tube facing upwards.

Preferably said elongate flow tube has a drain hole to enable fluid to drain into said chamber from said flow tube, said drain hole positioned at a low point of said flow tube and said flow tube configured so that the fluid within the flow tube flows toward said drain hole.

Preferably said elongate flow tube has an air bleed aperture located on a top surface to aid filing of the chamber.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

Figure 1:
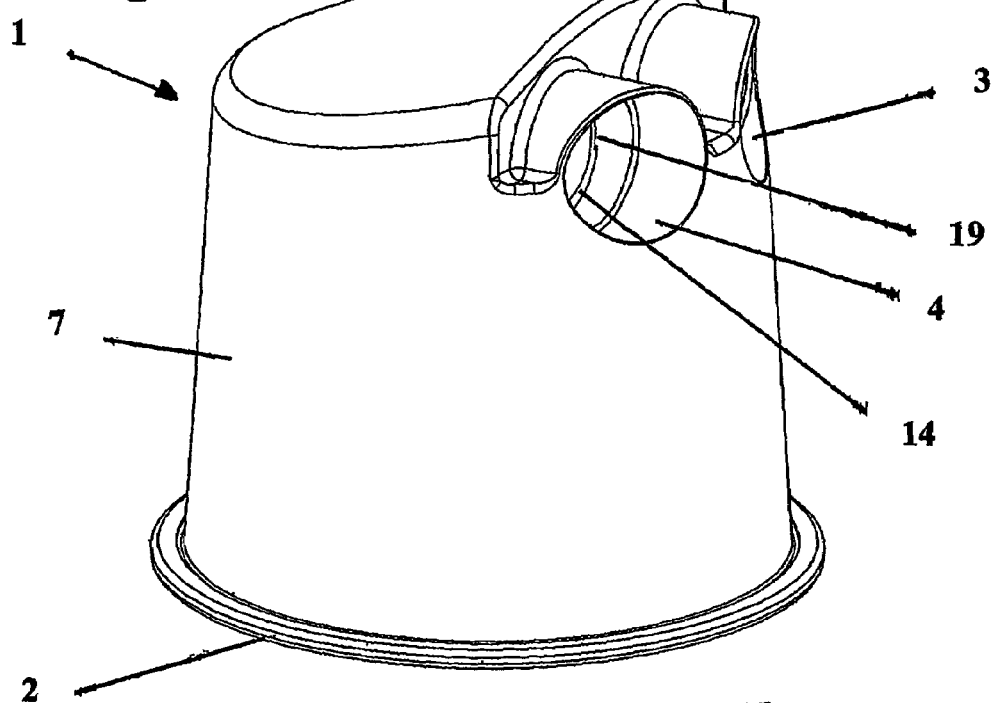
FIG. 1 is a perspective view of a water chamber according to one preferred embodiment of the present invention.
Figure 2:
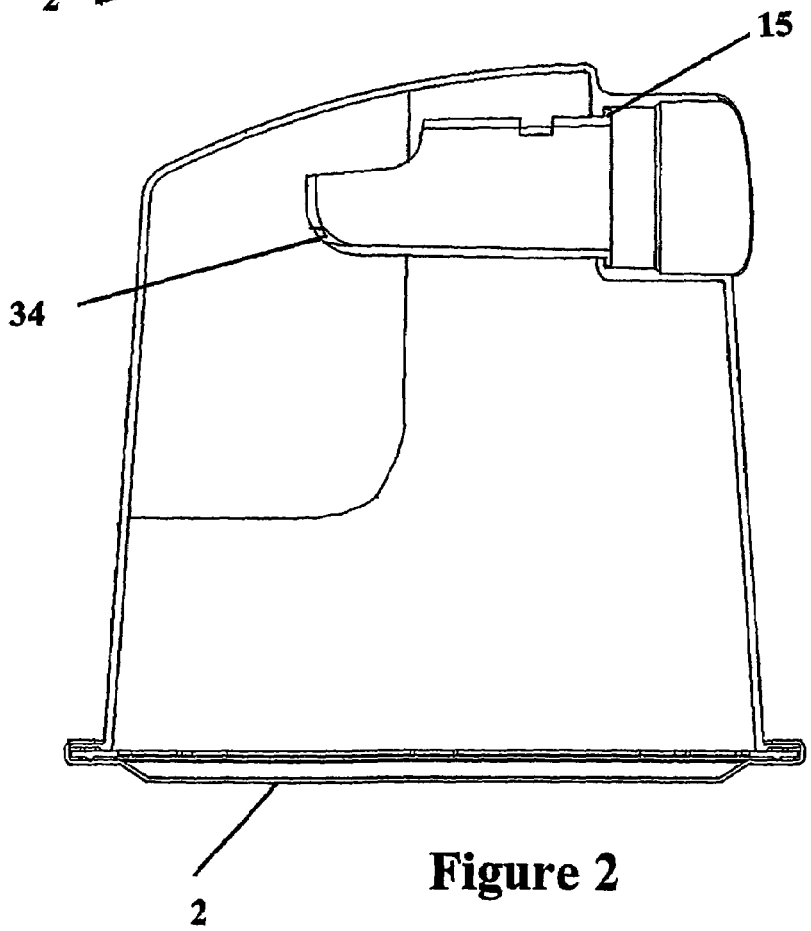
FIG. 2 is a cross sectional side elevation of the chamber of FIG. 1.
Figure 7:
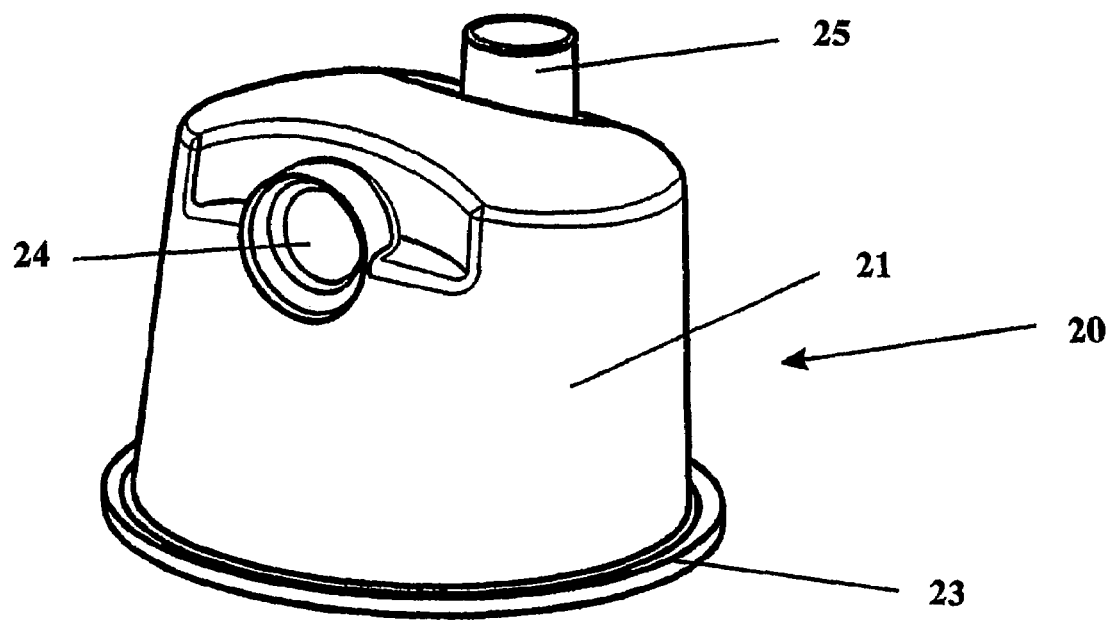
FIG. 7 is a perspective view of a water chamber according to an alternative preferred embodiment of the present invention.

For ease of reference the following describes the present invention applied to a water chamber for fitting to a CPAP machine. It is to be understood however, that the present invention is generally applicable to any humidification device which includes a removable water chamber. Referring to FIGS. 1 and 7, two types of water chamber suitable for application in a CPAP machine, or an in-line humidifier, are illustrated. The chambers are particularly adapted for use in machines adapted to receive slide-on chambers which make gases inlet or gases inlet and/or gases outlet connections to the chamber in the same slide-on motion.

The chamber 1 illustrated in FIG. 1, is constructed from an open bottomed plastic container 7 enclosed by a heat conductive base 2, and includes a horizontally aligned gases inlet 3 and a substantially parallel gases outlet 4. With reference to FIGS. 1 to 4, the water chamber of the present invention preferably includes an inlet extension tube 5, and an outlet extension tube 6, extending inwardly into the chamber interior from the periphery of the chamber wall and preferably having a generally tapering body. The inlet extension tube 5 and the outlet extension tube 6 are preferably moulded from the same clear thermoplastic material as the chamber shell 7.

The inclusion of an inlet/outlet extension tube has been found to significantly reduce noise produced by the airflow around the chamber. However at high flow rates, it is possible for water droplets or splashes to become entrained in the air flow and be carried out the chamber outlet. This is especially possible when the water chamber contains a large amount of liquid and the water surface is closer to the chamber outlet. This situation has the potential to become more problematic if the outlet port of the CPAP machine or in-line humidifier is disconnected from the patient delivery conduit, lowering the circuit resistance and resulting in significantly higher flow rates. Further, without the delivery conduit connected, any liquid entrained in the gases flow may be ejected directly from the humidification apparatus. This difficulty is alleviated in chambers incorporating the present invention.

In use, air is received into the chamber via inlet port 3 and travels down the inlet extension tube 5. On exiting the upwardly facing outlet 11 of the inlet extension tube 5, the gases flow is directed away from the surface of the water in the chamber, minimising the potential for splashing or water entrainment to occur. As the gases flow enters the chamber it is deflected off the roof of the chamber and is humidified by the evaporation of water from the water supply. Humidified air flows from the chamber through the upwardly facing inlet 12 of the outlet extension tube 6 and exits through outlet port 4. The upwardly orientated inlet 12 of the outlet extension tube 6 eliminates the direct path splashes might have from the surface of the water, into the outlet port 4. A drain hole 34 is provided in the bottom of the extension tubes to enable water to drain back into the chamber after filling, or built up condensation or splashes to drain during use. Preferably the shape and orientation of the extension tube and the position of the drain hole are such that the drain hole is at the lowest point and fluid flows toward the drain hole and back into the chamber.

The extension tubes are shaped to minimise the internal pressure losses of the gases flowing through the chamber in order to improve the efficiency of the chamber according to the present invention. The end of the extension tube furthest from the side of the chamber is shaped in a smooth curve to minimise the resistance to the gases flow.

Figure 3:
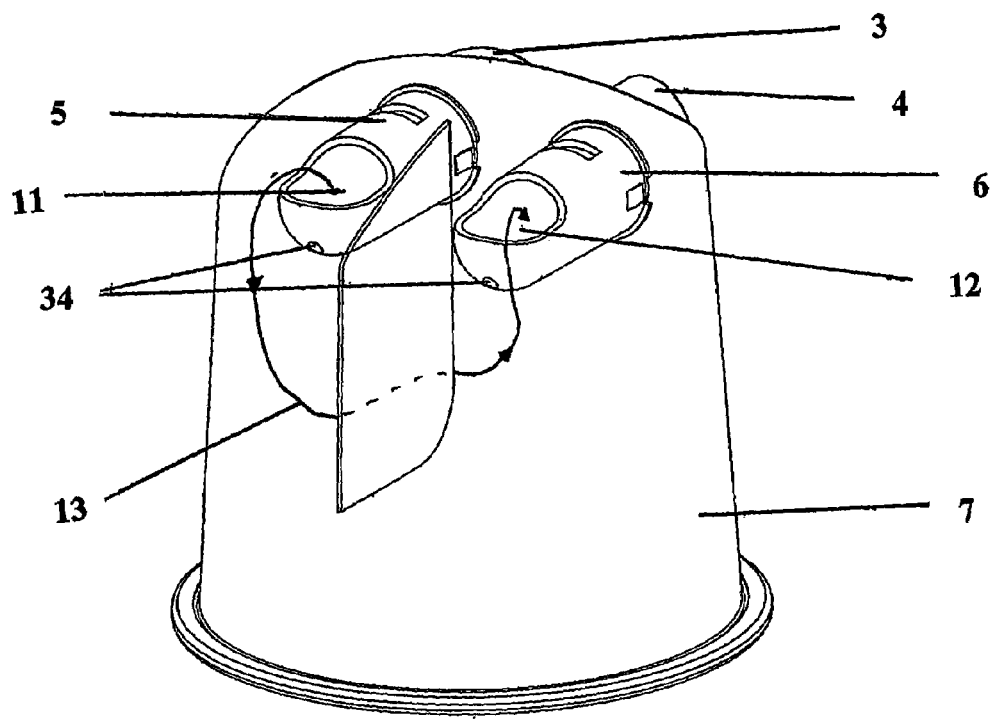
FIG. 3 is a perspective view of the water chamber of FIG. 1, showing the inner detail of the chamber.

The present invention may further include a downwardly extending central baffle or rib located between the inlet and outlet extension tubes to ensure against gases short circuiting the chamber by flowing directly from the exit 11 of the inlet extension tube, to the entry 12 of the outlet extension tube. With the baffle present the gases are forced to follow a more tortuous path ensuring adequate humidification during their journey through the chamber but without increasing the pressure losses in the chamber to an unacceptable level. The baffle preferably extends downwards from the roof of the chamber, and inwards from the portion of the chamber wall opposite the inlet/outlet ports. Preferably the size of the baffle is such that it not only ensures that the gases flow follows a tortuous path through the chamber, but also provides an additional barrier to splashes entering the inlet 12 of the outlet extension tube 6. The risk of splashes entering the extension tubes is highest when the water level is highest, the baffle may extend downwards such that it terminates below the water line when the chamber is full. The above described gases flow path is illustrated in FIG. 3 by the arrow 13.

Alternatively, it is envisaged that the direction in which the outlet of the inlet extension tube and/or the inlet of the outlet extension tube faces could be varied in order to achieve different results. For example the openings at the inner end of the extension tubes may be rotated about the axis of the extension tube to face in any direction. Further, the direction in which the openings of the inlet and outlet tubes face, may not be the same. Such arrangements (as for example facing mutually away) may be particularly suited for reducing the potential for splashes, and reducing the potential for splashes to enter the opening of the extension tubes when the baffle is present.

Figure 4:
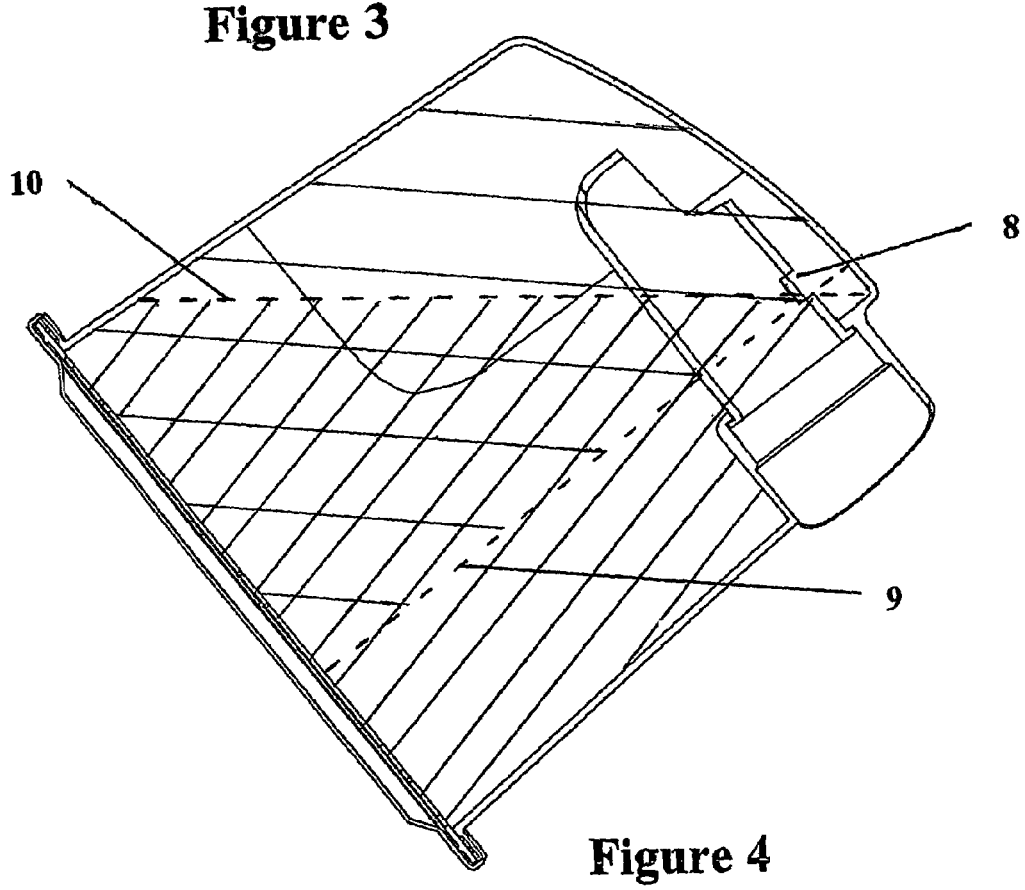
FIG. 4 is a cross sectional side elevation of the chamber of FIG. 1 in use with water therein and in a tilted condition demonstrating the operation of the inlet extension tube 5 in reducing the capacity for leakage through the gases inlet 3.

Preferably at least one extension tube has an air bleed aperture to aid filling of the chamber with the chamber tipped up. The air bleed is preferably located in the top surface of the extension tube and preferably toward the end of the extension tube which is connected to the chamber wall. Referring to FIG. 4, preferably the air bleed aperture 8 is positioned such that when the tank is tipped up for filling, the air bleed valve height corresponds with the preferred fill height 9 for the water chamber. This feature aids in preventing overfilling of the water chamber.

Additionally, the extension tubes 5 and 6 may act as a weir against water flow back through the gases inlet and gases outlet, upon tilting of the chamber as shown by water level line 10. The air bleed aperture 8 may be present only on the outlet extension tube 6 and not present in the inlet extension tube 5. This prevents water back-flow through the inlet port 3 occurring upon tilting of the chamber. However, this would also mean the inlet and outlet extension tubes are not interchangeable and will require additional tooling to manufacture.

Although the preceding description gives details of preferred embodiments having parallel and adjacent circular inlet/outlet ports, it is envisaged that other configurations are possible without departing from the spirit of the invention. For example the inlet/outlet ports of the chamber and connection manifold may have a non-circular cross section and/or not be symmetrical.

For ease of assembly the inlet and outlet extension tubes are preferably provided as a snap fit to their respective water chamber inlet or outlet, so that they can be pushed into the chamber through the inlet or outlet and, upon application of sufficient force, snap into a substantially watertight and secure condition.

Figure 5:
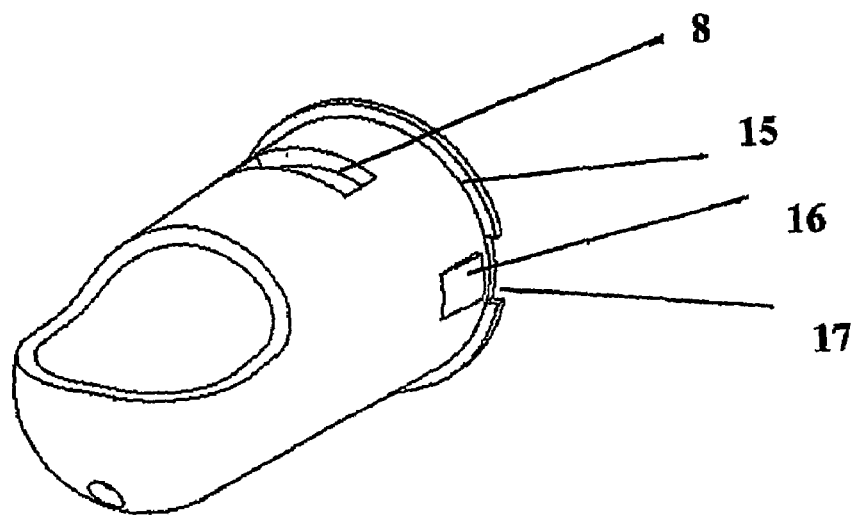
FIG. 5 is a perspective view of an extension tube according to the preferred embodiment of the present invention.
Figure 6:
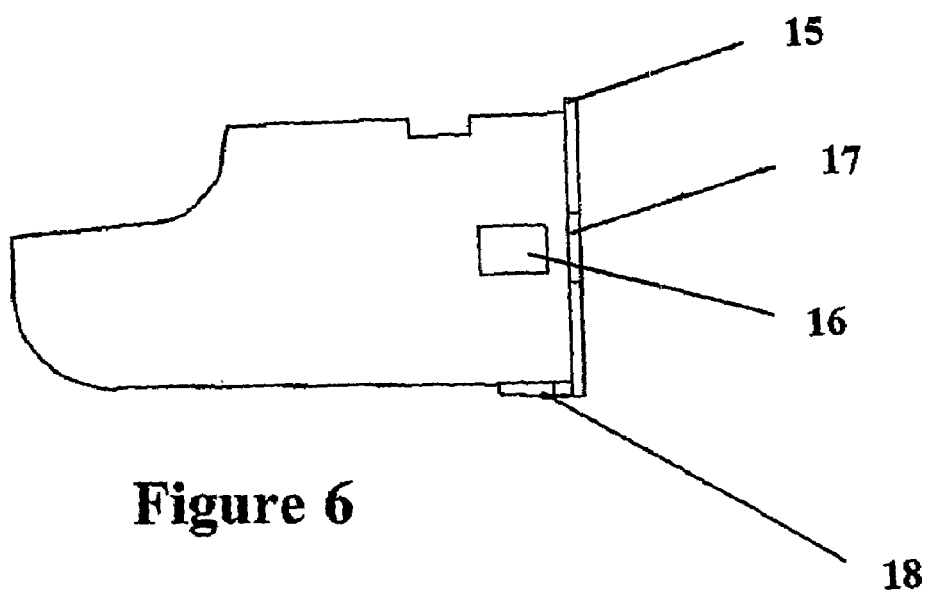
FIG. 6 is a side elevation of an extension tube according to the preferred embodiment of the present invention.

To this end the inlet 3 and outlet 4 ports of the water chamber may be provided with an inwardly perpendicularly extending annular flange 14 at the inner end thereof and the inlet/outlet extension tubes may include similar perpendicularly outwardly extending flanges 15 from one end of the generally tapering tubular body as illustrated in FIGS. 5 and 6. The flanges act together as sealing flanges in the fitted and assembled condition. To retain the extension tubes in the assembled condition, against both translational and rotational movement several securing mechanisms may be provided. In each case the securing mechanisms may be provided on either of the inlet/outlet (of the chamber) or the inlet/outlet extension tube. However it is preferred that they be on the extension tubes, as both components are intended for injection moulding and injection moulding of certain protrusions on the inner surface of the chamber inlet/outlet would be considerably more difficult than on the outer surface of the extension tubes. To secure the tubes against translational movement, and in a sealing condition between the sealing flanges, a plurality of retaining clip protrusions 16 may be provided spaced around the circumference of the tubular body of the extension tubes which co-operate with the inlet/outlet flange 14. Particularly for ease of manufacture, and ensuring a simple two part injection mould, a notch 17 is allowed in the flange 15 of the extension tubes adjacent the protrusion 16.

To retain the extension tubes against rotational movement when snap fitted into location, one or more locating protrusions 18 may be provided circumferentially distributed on the outer surface of the tubular body adjacent and contiguous with the outwardly and perpendicularly extending flange 15. The locating protrusions 18 are preferably generally tapered in both the circumferential and axial direction. Complementary notches 19 are provided in the inwardly extending flanges 14 of the chamber inlet and outlet. In fitting the extension tubes, the protrusions 18 are aligned with the notches 19, and upon full insertion of the tubes, the protrusions 18 enter into a tight frictional fit with the notches 19 ensuring substantial if not complete sealing. It will be appreciated that the mechanism employed to ensure proper location and sealing of the extension tubes into the water chamber may take many forms. Many alternatives will suggest themselves to persons skilled in the art such as glued joints, various forms of plastic welding and various configurations of clipping means and protrusions. The above description is of one particular preferred embodiment and is not meant to be in any way limiting.

It will be readily appreciated that the construction of the water chamber as described is simple to manufacture and each of the plastic components is itself capable of simple injection moulding. Consequently a water chamber according to the present invention is, while providing significant advantages, not significantly more expensive than existing chambers.

The chamber 20 illustrated in FIG. 7 is a variant of the chamber 1 previously described, and it will be appreciated that the chamber 20 functions in substantially the same manner as chamber 1. Chamber 20 has a transparent plastic shell 21 and a heat conductive base 22. The shell 21 and heat conductive base 22 are connected at a peripheral flange 23 which also serves as a securing flange in the slide-on connection with the CPAP machine in a similar manner as for chamber 1 already described. The chamber 20 includes a horizontally aligned gases inlet 24 which in use fits over a blower nozzle of the CPAP machine. A gases outlet 25 is provided in the roof of the chamber 20. The gases outlet 25 may be adapted to take standard breathing circuit fittings.

Figure 8:
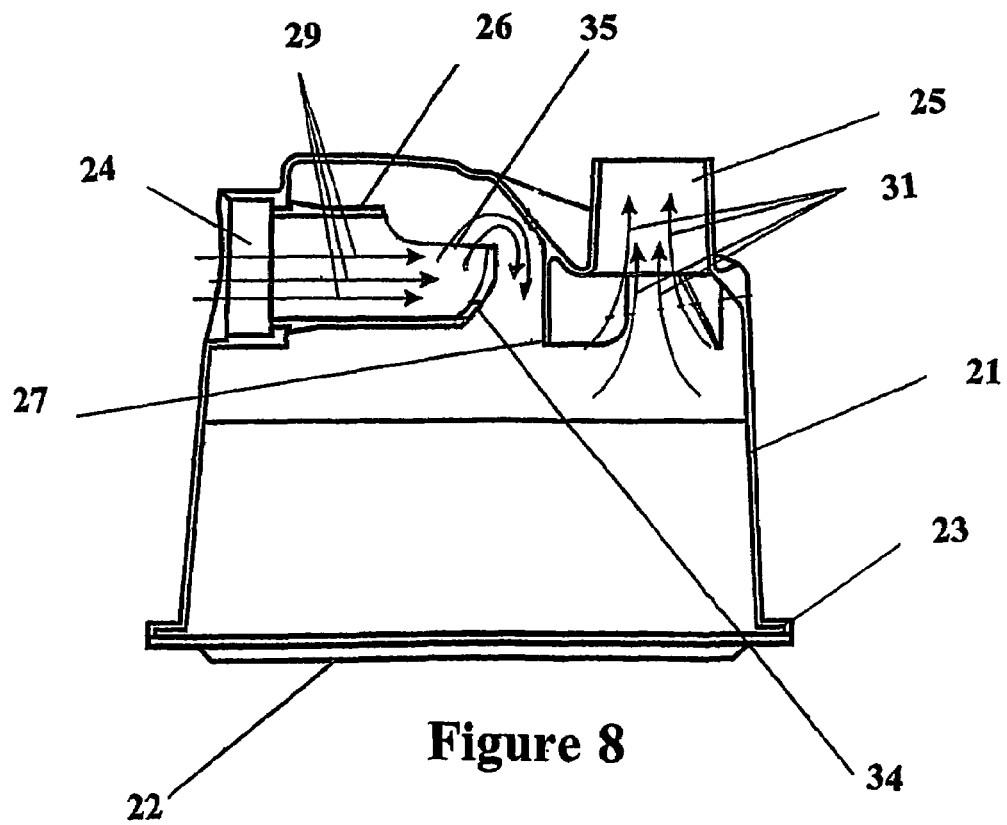
FIG. 8 is a cross sectional side elevation of the chamber of FIG. 7.

Referring to FIG. 8 the water chamber 20 is shown in cross section. In the present invention the water chamber 20 includes an inlet extension tube 26 extending inwardly into the chamber interior from the periphery of the gases inlet 24. In the most preferred embodiment the chamber further includes a curved downwardly extending baffle 27 located between the gases outlet 25 and the termination of the inlet extension tube 26 to ensure against gases short circuiting the chamber by flowing directly from the extension 26 to the outlet 25. The lower edge 28 of the baffle 27 preferably extends lower than the lower edge of the inlet extension tube 26. With the baffle 27 in place the gases are forced to follow a more tortuous path ensuring adequate humidification during their journey through the chamber 20.

In use air is received from the blower of the CPAP machine, or if the chamber is used in a standard humidification circuit, then from the ventilator, through inlet 24. Travelling through the inlet extension tube 26 the air is imparted with a more controlled laminar flow than is generally provided by the blower, as indicated by arrows 29. On exiting the upwardly facing outlet 35 of the inlet extension tube 26, the gases flow is directed away from the surface of the water in the chamber, minimising the potential for splashing to occur and forcing the gases flow to follow a more tortuous path. Air eventually leaves the chamber through outlet 25 as indicated by arrows 31.

A drain hole 34 is provided in the bottom of the extension tube 26 to enable water to drain back into the chamber after filling, or built up condensation or splashes to drain during use. Preferably the shape and orientation of the extension tube and the position of the drain hole are such that the drain hole is at the lowest point and fluid flows toward the drain hole and back into the chamber. Additionally, the inlet extension tube 26 acts as a weir against water flow back through gases inlet 24 upon tilting of the chamber 20. The construction and function of the inlet extension tube 26 is substantially the same as that described earlier as applied to chamber 1.

For ease of assembly the extension tube 26 is preferably provided as a snap fit to the inlet 24, so that it can be pushed into the chamber through the inlet 24 and, upon application of sufficient force, snap into a substantially watertight and secure condition. The details of how the inlet extension tube 26 is fitted to the chamber 20 are substantially the same as described earlier.

The invention claimed is:

1. A water chamber adapted for use in conjunction with a heater base and having at least one horizontally oriented gases port in a wall thereof the improvement comprising an elongate flow tube having a longitudinal axis which extends into said water chamber from the inner periphery of said at least one gases port with an opening at a distal end of said flow tube being spaced from the wall of said chamber, said opening facing a direction transverse to the longitudinal axis of said tube at the distal end, said transverse direction not being downwards and said distal end of said tube being shaped in a smooth curve to provide a barrier to water.

2. A water chamber as claimed in claim 1, wherein said chamber includes an inlet gases port and an outlet gases port, both said inlet gases port and said outlet gases port including a said elongate flow tube.

3. A water chamber as claimed in claim 2, wherein said chamber further includes a baffle between said opening of said inlet gases port tube and said opening of said outlet gases port tube.

4. A water chamber as claimed in claim 3, wherein said baffle extends from the roof of said chamber and terminates below the surface of water in said chamber when said chamber is filled to a maximum intended water level for use.

5. A water chamber as claimed in claim 2, wherein said inlet gases port and said outlet gases port includes a said elongate flow tube having an opening facing a direction transverse to an axis of said tube, said opening of said inlet flow tube and said opening of said outlet flow tube facing upwards.

6. A water chamber as claimed in claim 1, wherein said elongate flow tube has a drain hole to enable fluid to drain into said chamber from said flow tube, said drain hole positioned at a low point of said flow tube and said flow tube configured so that fluid within the flow tube flows toward said drain hole.

7. A water chamber as claimed in claim 1, wherein said elongate flow tube has an air bleed aperture located on a top surface to aid filing of the chamber.

* * * * *